(12) United States Patent
Pattanayak

(10) Patent No.: US 6,245,015 B1
(45) Date of Patent: Jun. 12, 2001

(54) PHOTOSONIC DIFFUSION WAVE-BASED TUMOR DETECTOR

(75) Inventor: Deva Narayan Pattanayak, Schenectady, NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/207,009

(22) Filed: Dec. 7, 1998

(51) Int. Cl.$^7$ ............................................. A61B 8/00
(52) U.S. Cl. ................................................. 600/438
(58) Field of Search .................. 600/407, 437, 600/438, 440, 442, 448, 458, 443

(56) References Cited

PUBLICATIONS

X.D. Li, T. Durduran, B. Chance, A.G. Yodh, D.N. Pattanayak, "Diffraction Tomography For Biomedical Imaging With DiffusePhoton Density Waves", SPIE Conference Society for Photo Illuminescent Engineering, 2/97.

Primary Examiner—George Manuel
(74) Attorney, Agent, or Firm—Donald S. Ingraham; Douglas E. Stoner

(57) ABSTRACT

Optical diffusion waves are generated inside localized regions in highly scattering media such as human breast tissue by simultaneously using visible and near-infrared light and focusing ultrasound waves in localized regions. The vibrating tissue medium scatters the impinging light to produce intensity-modulated diffusion waves. The diffusion waves emanating from the insonified region have a frequency equal to the frequency (or a harmonic) of the ultrasound waves and detected at the boundary of the breast in order to acquire data for the density, absorption and scattering parameters in each localized region. A multiplicity of diffusion wave detectors arranged at the boundary of the breast detect scattered diffusion waves at a multiplicity of locations. Each diffusion wave detector comprises a photodetector whose output signals are fed to a detector which detects the amplitudes and phase of the diffusion waves. The amplitude and phase signal components of the diffusion waves are supplied to a processor which computes pixel values for display on a monitor.

18 Claims, 1 Drawing Sheet

PHOTOSONIC DIFFUSION WAVE-BASED TUMOR DETECTOR

FIELD OF THE INVENTION

This invention relates to systems for imaging human tissue using both ultrasound and light waves and, more particularly, to systems for imaging the interior of a highly scattering medium such as the human breast in a non-invasive manner using ultrasound to generate modulated optical intensity waves (diffusion waves).

BACKGROUND OF THE INVENTION

Visible and near-infrared light tomography has been used to image the interior of tissue media. Diffusion wave tomography has also been used to image tissue. Visible and near-infrared light tomography is limited to relatively small depths of penetration, e.g., on the order of a few millimeters in breast tissue, whereas diffusion wave tomography has relatively poor resolution, e.g., on the order of a centimeter in breast tissue. It would be an advance in the state of the art if a system were developed to overcome the foregoing disadvantages of the prior art. In particular, it would be highly desirable to use visible and near-infrared light to image inhomogeneities, such as tumors, in the interior of the human breast non-invasively with a high degree of spatial resolution.

SUMMARY OF THE INVENTION

A system which generates optical diffusion waves inside a localized region in a highly scattering medium such as human breast tissue by simultaneously using visible and near-infrared light and focusing ultrasound waves in localized regions of the breast. The sources of visible and near-infrared light each comprise at least one laser. The vibrating tissue medium scatters the light impinging thereon to produce intensity-modulated diffusion waves. The diffusion waves emanating from the insonified region have a frequency equal to the frequency of the ultrasound waves (or a harmonic thereof). The resulting diffusion waves are detected at the boundary of the breast and are processed to acquire data on the absorption and scattering parameters of the insonified region. In accordance with one preferred embodiment, one or more diffusion wave detectors are arranged at the boundary of the breast to detect scattered diffusion waves at respective locations. Each diffusion wave detector comprises an optical-to-electrical transducer, i.e., a photodetector, such as a photomultiplier tube or a photodiode. The output signal of each diffusion wave detector is in turn fed to a detector which detects the amplitude and phase of the diffusion waves. Then the amplitude and phase signal components are fed to a processor which computes pixel values for display on a monitor.

The amplitude and phase of the scattered diffusion waves are proportional to the density/composition of the insonified region. Thus, by scanning different regions within the tissue by ultrasound and recording the amplitude and phase of the scattered diffusion waves, it is possible to map out the density and composition of the interior of the highly scattering breast tissue. From the spectroscopic characteristics of these parameters at selected wavelengths in the visible and near-infrared (500 to 1,400 nm), the localized regions inside the breast can be classified as cancerous or benign tumors or healthy breast tissue.

DETAILED DESCRIPTION OF THE PREFERRED EMBODIMENTS

Figure 1:
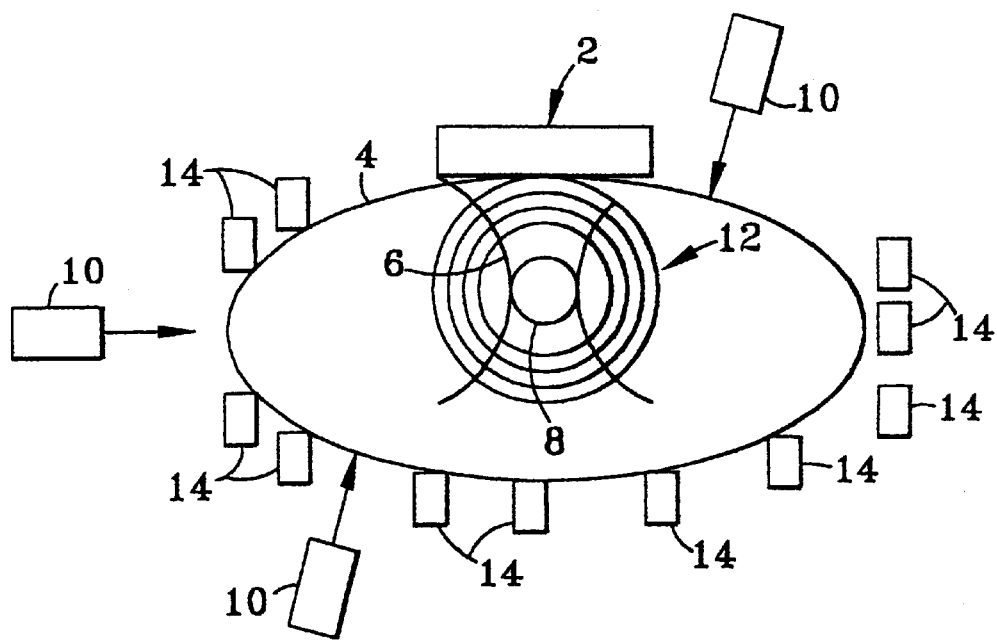
FIG. 1 is a schematic illustration of a photosonic diffusion wave-based tumor detection system as described herein.

In accordance with a preferred embodiment of the invention, a highly scattering medium such as a human breast is illuminated by light in the visible and near-infrared region. The transmitted light will penetrate and distribute inside the breast as if it were diffused into the inside of the tissue. The intensity of light waves inside the tissue will obey a diffusion-like wave equation, such as $$\left(\nabla^2 - \frac{3}{c^2}\frac{\partial^2}{\partial t^2} - \frac{1}{D^2}\frac{\partial}{\partial t} - 3\rho^2\sigma_a\sigma_{tr}\right)I_d(\vec{r},t) = \quad (1)$$

$$-\frac{3}{4\pi}\left(\frac{1}{c}\frac{\partial}{\partial t} + \rho\sigma_{tr}\right)S_o(\vec{r},t),$$

where $I_d(\vec{r},t)$ is the light intensity, c is the velocity of light in a vacuum, D is the diffusion constant. The diffusion constant D is given by $D^2=(c/3)\,l_d$, where $l_d=[\rho(\sigma_a+\sigma_{tr})]^{-1}$, $l_d$ is the diffusion mean free path, $\rho$ is the density of the medium, $\sigma_a$ is the absorption cross section and $\sigma_{tr}$ is the transport cross section. The transport cross section $\sigma_{tr}$ is in turn defined as $\sigma_{tr}=\sigma_s(1-\vec{u})+\sigma_a$, where $\sigma_s$ is the scattering cross section and $\vec{u}$ is the mean cosine of the scattering angle. The term $S_0(\vec{r},t)$ in Eq. (1) is the modulated intensity of the external light source. In this embodiment of the invention, the external light source is not modulated and is a constant. For this situation, the right-hand side of Eq. (1) follows the time dependence of the density and scattering parameters, giving the following equation:

$$\left[\nabla^2 - \frac{3}{c^2}\frac{\partial^2}{\partial t^2} - \frac{1}{D(\vec{r},t)^2}\frac{\partial}{\partial t} - 3\rho(\vec{r},t)^2\sigma_a\sigma_{tr}(\vec{r},t)\right]I_d(\vec{r},t) = \quad (2)$$

$$-\frac{3}{4\pi}\rho(\vec{r},0)\sigma_{tr}(\vec{r},t)S_o(\vec{r}).$$

In utilizing this technique, an ultrasound beam is focused into a localized region inside the breast. The ultrasound waves perturb the density of the tissue in that region and also the scattering coefficient by modulating the size of the cells or constituents of the inhomogeneous medium. Density of the tissue varies as a function of the ultrasound waves in accordance with the equation:

$$\rho(\vec{r},t)=\rho(\vec{r},0)\nabla F(\vec{r})T(t)\cos(k\cdot\vec{r}-\omega_s t), \quad (3)$$

where the parameters F and T define the beam width and pulse width of the ultrasound and are essentially zero outside the focal region of the ultrasound waves.

Substituting Eq. (3) into Eq. (2) yields $$\left[\nabla^2 - \frac{3}{c^2}\frac{\partial^2}{\partial t^2} - \frac{1}{D(\vec{r},t)^2}\frac{\partial}{\partial t} - \right.$$
$$\left. 3[\rho(\vec{r},0)\nabla F(\vec{r})T(t)\cos(k\cdot\vec{r} - \omega_s t)]^2 \sigma_a\sigma_{tr}(\vec{r},t)\right]I_d(\vec{r},t) =$$
$$-\frac{3}{4\pi}\rho(\vec{r},0)\sigma_{tr}(\vec{r},t)S_o(\vec{r})\nabla F(\vec{r})T(t)\cos(k\cdot r - \omega_s t)$$

(4)

Equation (4) clearly points out the mechanism for the origin of the diffusion waves by means of the ultrasound waves. The intensity of the laser light varies as a function of the ultrasound frequency and this variation in light intensity constitutes the diffusion waves emanating from the region at which the ultrasound beam is focused. Because of the self-interaction of these waves, harmonics of the diffusion waves also emanate from the insonified region.

The basic structure of a system for carrying out this technique is shown in FIG. 1. An ultrasound transducer array 2 is sonically coupled to a highly scattering medium 4, such as breast tissue, and transmits ultrasound waves 6 which are focused in a localized region 8. The ultrasound beam frequency is preferably on the order of several megahertz which is selected to minimize attenuation in highly scattering medium 4. At the same time, medium 4 is illuminated by light from a plurality of incoherent sources or from a plurality of laser sources 10. The light sources are placed so that light enters the highly scattering medium 4 from different directions.

The light which penetrates insonified region 8 is modulated by ultrasound waves 6 and emanates from the insonified region in the form of diffusion waves 12. In contrast, light waves which penetrate regions unperturbed by the ultrasound waves are not modulated to form diffusion waves. A multiplicity of diffusion wave detectors 14, placed around the boundary of highly scattering medium 4, are used to detect diffusion waves 12. The strength of the diffusion waves is a function of ultrasound intensity and light intensity, but more importantly is a function of the absorption and scattering coefficients of insonified region 8. By using light sources of different wavelengths (in the visible and near-infrared regions, i.e., 500 nm–1,400 nm), it is possible to record the absorption and scattering coefficients of the insonified region. If the insonified region is a tumor, the absorption and scattering properties of the tumor can be used to determine whether the tumor is benign or cancerous since the absorption and scattering coefficients of cancerous tissue are different than those of benign tissue in the near-infrared region.

In practicing this technique, reflected and diffracted diffusion waves can be suppressed by collecting those diffusion waves that originate from the region where the ultrasound beam is focused. The signal-to-noise ratio will be high because without the ultrasound waves, diffusion waves are not present, whereas in the presence of the ultrasound waves, diffusion waves are created corresponding to the frequency of the ultrasound waves and harmonics thereof.

Figure 2:
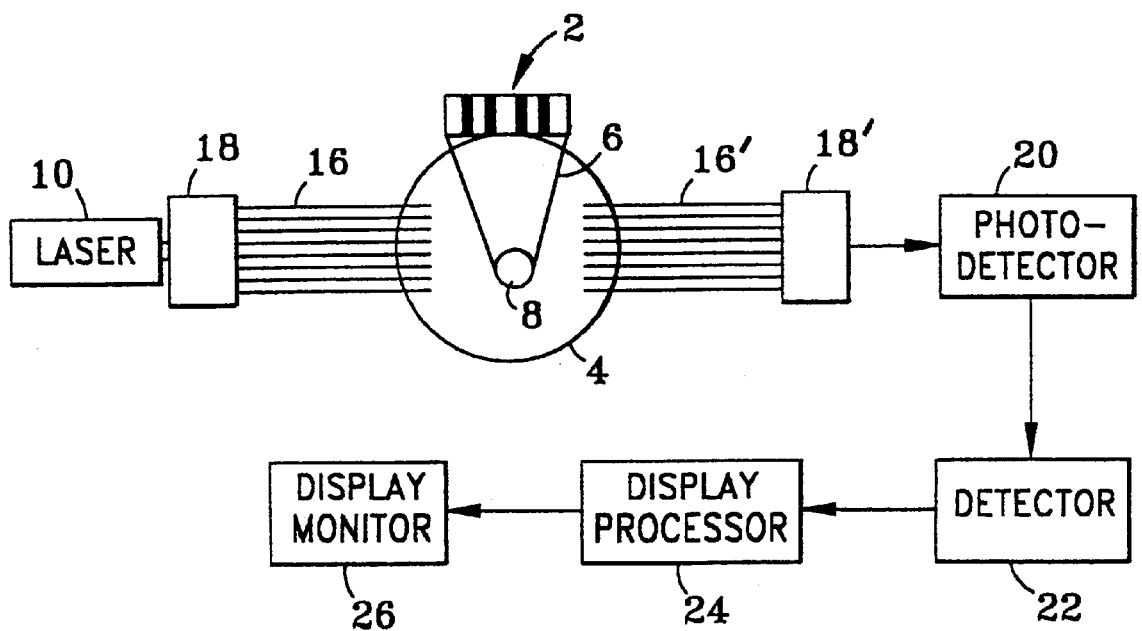
FIG. 2 is a schematic illustration of a portion of a photosonic diffusion wave-based tumor detection system in accordance with one preferred embodiment of the invention.

A portion of the tumor detection system in accordance with a preferred embodiment of the invention is depicted in FIG. 2. A laser 10 is optically coupled to a first multiplicity 16 of optical fibers by means of a first fiber coupler 18. The distal ends of the optical fibers of the first multiplicity 16 are placed in contact with the breast or other highly scattering medium 4 such that laser light is directed toward region 8 where the ultrasound beam transmitted by transducer array 2 is focused. A photodetector 20 is optically coupled to the breast tissue through a second multiplicity 16' of optical fibers and a second fiber coupler 18'. The distal ends of the optical fibers of the second multiplicity 16' are placed in contact with the breast such that the scattered diffusion waves emanating from insonified region 4 are detected by photodetector 20. The photodetector transduces the diffusion waves into electrical signals which are supplied to a detector 22. Detector 22 comprises a conventional mixer for forming in-phase (I) and quadrature (Q) components and circuitry for determining amplitude and phase of the diffusion waves from the I and Q components. The amplitude and phase of the diffusion waves are related to the density and the absorption and scattering coefficients of the tissue in the insonified region. The amplitude and/or phase information is provided to a display processor 24 which converts the data into pixel information suitable for display on a display monitor 26. An amplitude and/or phase image of the interior of the breast can be synthesized or constructed by scanning the ultrasound focal region to cover the interior of the breast.

Although FIG. 2 depicts only a single laser light and a single photodetector, it will be appreciated that the system preferably comprises multiple light sources and multiple photodetectors. The output signals of the multiple photodetectors can be summed before or after detection of the amplitude and phase of the diffusion waves by applying appropriate time delays as a function of the distance of propagation from the insonified region to the respective photodetector.

The frequency of the laser light is selected to provide spectroscopic differences in the visible and near-infrared regions (500 nm–1,400 nm) between different tissue types. In particular, the use of different optical wavelengths for the transmitted light enables differentiation of different types of cancerous and non-cancerous tissues because the optical scattering parameters of cancerous and non-cancerous tissues are different. This appears as a color parameter in the final reconstruction, helping to discriminate normal tissue from abnormal and cancerous tissue.

The resolution obtained by the above-described process can be enhanced by use of an image reconstruction procedure. In reconstructing the sources of the diffusion waves, i.e., the insonified regions, a near-field reconstruction procedure can be employed which incorporates the so-called evanescent waves and window functions to limit the growth of side lobes. Essentially the approach is as follows: (1) measure the diffusion wave phase and amplitudes at a plane far from the insonified region; (2) take a windowed cosine transform (Fourier transform) to obtain the angular spectrum amplitude; (3) filter out evanescent wave propagation factors; and (4) take a windowed cosine transform. This results in reconstruction of the scattering parameters of the insonified region. The ultrasound beam is scanned over different portions and the foregoing procedure is repeated to obtain a picture of the whole interior of the breast. Alternatively, finite differential element technique can be used for source reconstruction.

Thus a system and a method for light-based and ultrasound-based non-ionizing and non-invasive imaging of tumors inside a human breast or of an inhomogeneous region inside a highly scattering medium, has been described. The system uses scattered light and pulsed ultrasound. The technique employed is not based on the phase of the coherent light inside the tissue. The system can image tumors deep inside the tissue illuminated by scattered (diffused) light and insonified by pulsed ultrasound waves.

By properly choosing the ultrasound frequency, tissue penetration of about 10 cm can be achieved in breast tissue. Coherent light sources are also not necessary as the technique uses diffused or scattered light and generates optical diffusion waves at different localized regions inside the breast by focusing pulsed ultrasound in those localized regions. The phase and amplitudes of these coherent optical diffusion waves are measured using detectors situated at the surface of the breast or scattering medium.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A method for detecting a property in an interior of a mass of tissue, comprising the steps of:

focusing an ultrasound beam having an ultrasound frequency at a localized region in the mass of tissue during one detection cycle;

directing a first beam of light of unmodulated intensity and having a first light frequency into the mass of tissue during said one detection cycle;

detecting diffusion waves of said ultrasound frequency emanating from the mass of tissue during said one detection cycle;

focusing said ultrasound beam having said ultrasound frequency at said localized region during a second detection cycle;

directing a second beam of light unmodulated in intensity and having a second light frequency different than said first light frequency into the mass of tissue during said second detection cycle; and detecting diffusion waves of said ultrasound frequency emanating from the mass of tissue during said second detection cycle.

2. The method as defined in claim 1, further comprising the step of determining amplitudes of the detected diffusion waves.

3. The method as defined in claim 2, further comprising the step of displaying as an image a function of said amplitudes of said detected diffusion waves.

4. The method as defined in claim 1, further comprising the step of determining phase of the detected diffusion waves.

5. The method as defined in claim 4, further comprising the step of displaying as an image a function of said phase of said detected diffusion waves.

6. The method as defined in claim 1, wherein the step of detecting diffusion waves comprises transducing said diffusion waves of said ultrasound frequency into electrical signals.

7. The method as defined in claim 1, further comprising the steps of repeating said focusing, directing and detecting steps for each one of a multiplicity of localized regions in the mass of tissue.

8. The method as defined in claim 1 wherein the first light frequency is within the range of about 500 to 1,400 nanometers.

9. A method for detecting a property in an interior of a mass of tissue, comprising the steps of:

focusing an ultrasound beam having an ultrasound frequency at a localized region in the mass of tissue during one detection cycle;

directing a first beam of light of unmodulated intensity and having a first light frequency into the mass of tissue during said one detection cycle;

directing a second beam of light unmodulated in intensity and having a second light frequency different than said first light frequency into the mass of tissue during said one detection cycle; and detecting diffusion waves of said ultrasound frequency emanating from the mass of tissue during said one detection cycle.

10. A system for detecting a property in an interior of a mass of tissue, comprising:

an ultrasound transducer array arranged and controlled to focus an ultrasound beam having an ultrasound frequency at a localized region in the mass of tissue during one detection cycle;

a light source having a first light frequency and arranged to direct a first beam of light of unmodulated intensity into the mass of tissue during said one detection cycle;

a diffusion wave detector arranged to detect diffusion waves of said ultrasound frequency emanating from the mass of tissue during said one detection cycle; and a second light source having a second light frequency different than said first frequency and arranged to direct a second beam of light of unmodulated intensity into the mass of tissue during said one detection cycle.

11. The system as defined in claim 10, further comprising an amplitude detector operatively coupled to said diffusion wave detector for determining amplitudes of the detected diffusion waves.

12. The system as defined in claim 11, further comprising a display monitor for displaying as an image a function of said amplitudes of said detected diffusion waves.

13. The system as defined in claim 10, further comprising a phase detector operatively coupled to said diffusion wave detector for determining phase of the detected diffusion waves.

14. The system as defined in claim 13, further comprising a display monitor for displaying as an image a function of said phase of said detected diffusion waves.

15. The system as defined in claim 10, wherein said diffusion wave detector comprises a photodetector.

16. The system as defined in claim 10, wherein said light source comprises a laser.

17. The system as defined in claim 10 wherein each of said first and second light frequencies is within the wavelength range of 500 to 1,400 naometers.

18. a system for detecting a property in an interior of a mass of tissue, comprising:

an ultrasound transducer array arranged and controlled to focus an ultrasound beam having an ultrasound frequency at a localized region in the mass of tissue during one detection cycle;

a light source having a first light frequency and arranged to direct a first beam of light of unmodulated intensity into the mass of tissue during said one detection cycle, wherein said light source comprises a source of incoherent light; and a diffusion wave detector arranged to detect diffusion waves of said ultrasound frequency emanating from the mass of tissue during said one detection cycle.

* * * * *